(12) United States Patent
Van Der Beek et al.

(10) Patent No.: US 9,050,451 B2
(45) Date of Patent: Jun. 9, 2015

(54) ELECTRODE ASSEMBLY WITH MAGNETIC CONNECTION

(75) Inventors: Maurice Hubertus Elisabeth Van Der Beek, Eindhoven (NL); Arthur Robert Van Es, Eindhoven (NL); Sean Scott Wheelhouse, Orem, UT (US); Timon Rutger Grob, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 58 days.

(21) Appl. No.: 13/701,047

(22) PCT Filed: Apr. 27, 2011

(86) PCT No.: PCT/IB2011/051857
§ 371 (c)(1),
(2), (4) Date: Nov. 30, 2012

(87) PCT Pub. No.: WO2011/151742
PCT Pub. Date: Dec. 8, 2011

(65) Prior Publication Data
US 2013/0066412 A1    Mar. 14, 2013

Related U.S. Application Data

(60) Provisional application No. 61/351,083, filed on Jun. 3, 2010.

(51) Int. Cl.
*A61B 5/0408* (2006.01)
*A61B 5/0416* (2006.01)
(Continued)

(52) U.S. Cl.
CPC ............ *A61N 1/0472* (2013.01); *A61B 5/0456* (2013.01); *A61B 5/0472* (2013.01); *A61B 5/048* (2013.01); *A61B 5/0452* (2013.01);
*A61B 5/0492* (2013.01); *A61N 1/0408* (2013.01); *A61N 1/0452* (2013.01); *A61N 1/0456* (2013.01);
(Continued)

(58) Field of Classification Search
CPC .. A61B 5/0408; A61B 5/0416; A61B 5/0492; A61N 1/0472; A61N 1/048; A61N 1/0456; A61N 1/0492; A61N 1/0452
USPC ................... 600/391, 392, 394; 607/152, 153
See application file for complete search history.

(56) References Cited

U.S. PATENT DOCUMENTS

| | | | |
|---|---|---|---|
| 4,112,941 A | | 9/1978 | Larimore |
| 4,259,965 A | * | 4/1981 | Fukuda et al. ................ 600/392 |
| 4,270,543 A | * | 6/1981 | Tabuchi et al. ............... 600/396 |
| 4,653,503 A | * | 3/1987 | Heath ........................... 600/391 |
| 4,947,846 A | * | 8/1990 | Kitagawa et al. ............ 600/391 |

(Continued)

FOREIGN PATENT DOCUMENTS

| WO | 2009055397 A2 | 4/2009 |
|---|---|---|
| WO | 2009150440 A1 | 12/2009 |

*Primary Examiner* — Lee S Cohen

(57) ABSTRACT

An electrode assembly that includes an electrode configured to provide electrical contact with a subject's skin through a subject contact surface. The electrode includes an electrode base pad having a first contact surface on a side of the electrode opposite the subject contact surface. The electrode also includes a connector assembly configured to electrically connect the electrode to an external electrical apparatus to transfer electrical signals between the subject's skin and the external electrical apparatus. The connector assembly includes a housing having a second contact surface. The second contact surface is configured to be magnetically and electrically coupled to the first contact surface of the electrode base pad. The connector assembly also includes an electrical connector configured to connect the second contact surface to the external electrical apparatus.

15 Claims, 8 Drawing Sheets

(51) Int. Cl.
  *A61B 5/0492* (2006.01)
  *A61N 1/04* (2006.01)
  *A61B 5/0456* (2006.01)
  *A61B 5/0472* (2006.01)
  *A61B 5/048* (2006.01)
  *A61B 5/0452* (2006.01)

(52) U.S. Cl.
  CPC ............ *A61N 1/048* (2013.01); *A61N 1/0492* (2013.01); *A61N 1/0496* (2013.01)

(56) References Cited

U.S. PATENT DOCUMENTS

| | | | |
|---|---|---|---|
| 5,265,579 A * | 11/1993 | Ferrari | 600/385 |
| 6,418,333 B1 * | 7/2002 | Axelgaard | 600/391 |
| 7,079,884 B1 * | 7/2006 | Epstein | 600/391 |
| 7,522,951 B2 * | 4/2009 | Gough et al. | 600/388 |
| 2001/0027270 A1 | 10/2001 | Stratbucker | |
| 2009/0124847 A1 | 5/2009 | Doty et al. | |
| 2010/0049028 A1 | 2/2010 | Shin et al. | |

* cited by examiner

ELECTRODE ASSEMBLY WITH MAGNETIC CONNECTION

The invention relates to an electrode for use in medical applications (e.g., stimulations and physiological parameters monitoring), and a method of use therefor.

Electrodes that provide electrical contact with a patient's skin and that are electrically connected to medical devices via a connector assembly are known. However, such electrodes are typically connected to the connector assembly using a mechanical connection. For example, the electrodes typically have a male snap structure 10 (see FIG. 1a) configured to engage in a snap-fit connection with a female receiving portion 12 (see FIG. 1b) of the connector assembly. As such, the connection and disconnection of the electrodes to and from the connector assembly requires force. This may be problematic to users, such as the elderly, that use such medical devices in their home. It may also be difficult for users to connect the connector assembly to the precise location of the electrode, especially when the electrode is positioned behind the ear. These difficulties of connecting the connector assembly and the electrode may lead to improper connections. The improper connection between the electrodes and the connector assembly may result in suboptimal electrical contact, thus resulting in suboptimal distribution and/or reception of electric signals.

In addition, electrodes that are connected to connector assemblies with snap-fit connections typically have a male snap structure that consists of a metal eyelet and a metal stud. However, this configuration may create "hot spots" of high current density, or high-current concentrations at a specific location, that can lead to an irritating and/or uncomfortable burning sensation on the skin.

One aspect of the invention relates to an electrode assembly that includes an electrode configured to provide electrical contact with a subject's skin through a subject contact surface. The electrode includes an electrode base pad having a first contact surface on a side of the electrode opposite the subject contact surface. The electrode also includes a connector assembly configured to electrically connect the electrode to an external electrical apparatus to transfer electrical signals between the subject's skin and the external electrical apparatus. The connector assembly includes a housing having a second contact surface. The second contact surface is configured to be magnetically and electrically coupled to the first contact surface of the electrode base pad. The connector assembly also includes an electrical connector configured to connect the second contact surface to the external electrical apparatus.

Another aspect of the invention relates to a method for delivering electrical stimulation to a subject, monitoring a physiological parameter or such of the subject, or both. The method includes the step of connecting an electrode to the subject's skin. The electrode includes an electrode base pad having a first contact surface on a side of the electrode opposite the subject contact surface. The method also includes the step of coupling the first contact surface of the electrode base pad to a second contact surface of a connector assembly. The second contact surface is located on a housing of the connector assembly, and the coupling is provided by a magnet of either the first contact surface or the second contact surface. The method further includes the step of connecting the second contact surface of the connector assembly to an external electrical apparatus to transfer electrical signals between the subject's skin and the electrical apparatus. The connection is provided by an electrical connector of the connector assembly.

Another aspect of the invention relates to an electrode assembly having means for connecting an electrode to a subject's skin. The electrode includes an electrode base pad having a first contact surface on a side of the electrode opposite the subject contact surface. The electrode also includes means for coupling the first contact surface of the electrode base pad to a second contact surface of a connector assembly. The second contact surface is located on a housing of the connector assembly. The electrode further includes means for connecting the second contact surface of the connector assembly to an external electrical apparatus to transfer electrical signals between the subject's skin and the electrical apparatus.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 2:
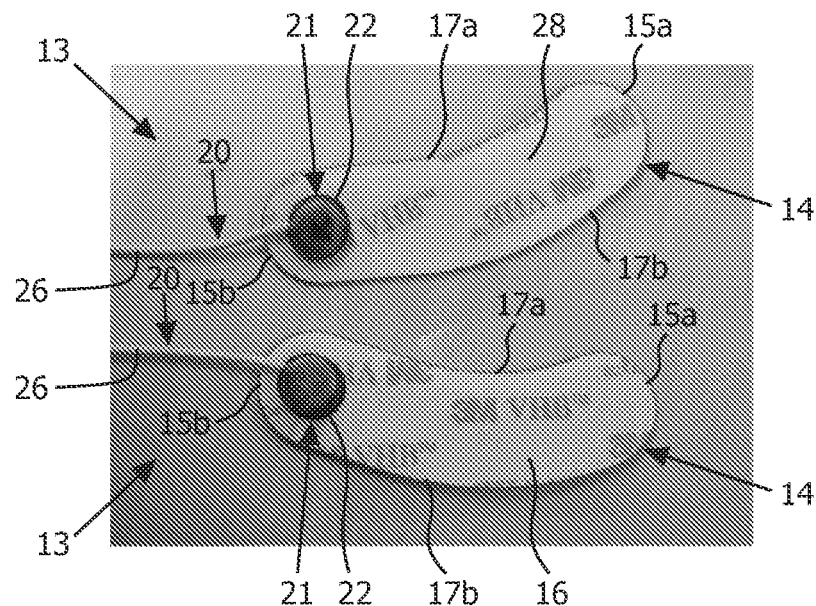
FIG. 2 illustrates a base pad of an electrode in accordance with one embodiment.
Figure 3A:
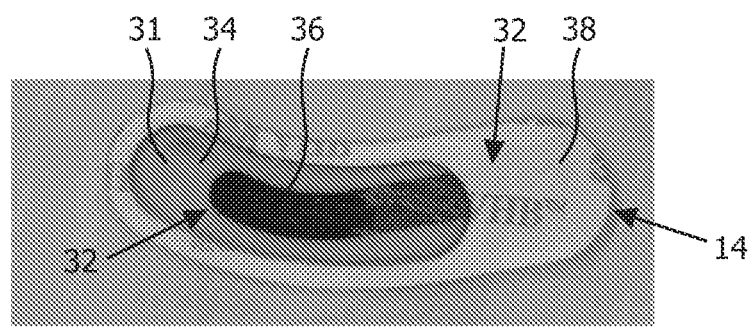
FIGS. 3a-3b illustrate a subject contact surface on a side of the electrode opposite the base pad and the base pad of the electrode, respectively, in accordance with one embodiment.
Figure 3B:
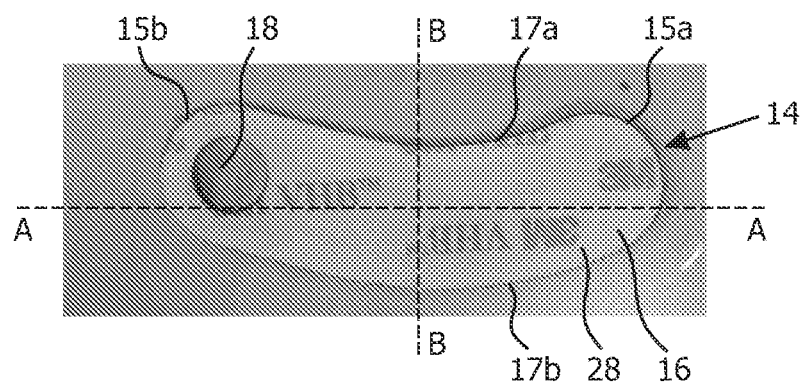

FIG. 2 illustrates an electrode assembly 13 that includes an electrode 14 for providing electrical contact with a subject's skin through a subject contact surface or skin contact surface 31 (see FIG. 3a). The electrode 14 includes an electrode base pad 16 having a first contact surface 18 (see FIG. 3b) on a side of the electrode 14 opposite the skin contact surface 31. The electrode assembly 13 also includes a connector assembly 20 configured to electrically connect the electrode 14 to an external electrical apparatus (not shown) such that electrical signals can be transferred between the subject's skin and the external electrical apparatus. The external electrical apparatus can be of any type of monitoring or stimulation devices, such as, just for example, electrograph (ECG) devices, electroencephalograph devices, electromyography devices, transcutaneous electrical nerve stimulation devices, electrical muscle stimulation devices, neuromuscular stimulation devices, or functional electrical stimulation devices. The connector assembly 20 includes an attachment structure 21 having a housing 22 and a second contact surface 24 (see FIG. 4).

The second contact surface 24 is configured to be magnetically and electrically coupled to the first contact surface 18 of the electrode base pad 16, as shown in FIG. 2. One or both of the first contact surface 18 and the second contact surface 24 may include a magnet. In one embodiment, either one of the first contact surface 18 or the second contact surface 24 may include a magnet and the other of the first contact surface 18 or the second contact surface 24 may include a metal material that is attracted to the magnet. Alternatively or additionally, the second contact surface 24 may be provided with a magnet. For example, the second contact surface 24 may be a magnet or the second contact surface 24 may be a metal material disposed on a magnet such that the second contact surface 24 may be magnetically and electrically coupled to the first contact surface 18 of the electrode base pad 16. Either one of the first contact surface 18 or the second contact surface 24 may include a ferromagnetic material, such as, just for example, iron, nickel, cobalt, rare earth metals, alloys (e.g., Alnico), or any combination thereof.

The housing 22 houses one or more components of the connector assembly 20. The housing 22 may be made of any suitable non-conductive material, including, just for example, any thermoplastic and/or elastomeric polymer such as polyvinyl chloride (PVC), thermoplastic polyurethanes, or fiber-reinforced polymer.

The connector assembly 20 also includes an electrical connector 26 configured to connect the second contact surface 24 to the external electrical apparatus. The electrode base connector 26 may be an electrical cable or wire capable of transmitting electric signals, such as a lead wire.

The configuration of electrode 14 shown and described above with first contact surface 18 being the only first contact surface, and/or being disposed opposite skin contact surface 31 is not intended to be limiting. For example, in one embodiment, electrode 14 includes a first contact surface formed on the same side of the electrode 14 as the skin contact surface 31. This first contact surface formed on the same side of electrode 14 as the skin contact surface 31 may replace the first contact surface 18 shown in the drawings and described above. The electrode 14 may include both of the first contact surface formed on the same side of electrode 14 as the skin contact surface 31 and first contact surface 18 shown in the drawings and described above.

In the embodiment of FIG. 2, the electrode 14 includes curves or smoothly rounded bends that generally form a banana shape. That is, the electrode 14 may be rounded at ends 15a, 15b with arcuate sides 17a, 17b that form a generally arcuate body. Arcuate does not necessarily mean a perfect arc, but may refer to general curvature of the sides and/or body as a whole. The rounded ends 15a, 15b may connect with the arcuate sides 17a, 17b in a smooth manner (i.e., without edges). In the embodiment shown in FIG. 3b, the ends 15a, 15b are generally curved in a convex shape away from latitudinal line B-B. In the illustrated embodiment, the arcuate side 17a is generally curved towards longitudinal line A-A in a concave shape and the arcuate side 17b is generally curved away from longitudinal line A-A in a convex shape. The curvature of the arcuate sides may vary along the length of the body. For example, in some embodiments, the arcuate sides may be defined by multiple curves or bends having various angles so that the arcuate sides 17a, 17b are spaced at different distances from each other along the length of the body. In such embodiments, the length or angle of curvature of the ends 15a, 15b may be different from one other. In some embodiments, the arcuate sides 17a, 17b of the arcuate body may be longer than the rounded ends 15a, 15b, thus forming a generally longitudinally extending body. However, the above description of the configuration, shape, and size of the electrode 14 is not intended to be limiting, and it is contemplated that the configuration, shape, and size of the electrode 14 may vary in other embodiments.

The banana-shaped configuration of the electrode 14 shown in FIG. 2 may facilitate the positioning of the electrode 14 at various positions on the subject's body. For example, the curved banana-shape of the electrode 14 in one embodiment can facilitate the positioning of the electrode 14 behind the subject's ear, which is usually difficult due to the fact that one cannot easily see the side of one's head when attempting to apply the electrode 14 to the side of the head. However, it is contemplated that the electrode 14 may have other shapes, such as just, for example, circular, oval, or rectangular, and may have various sizes.

In one embodiment, the electrode base pad 16 forms a generally flat back surface 28 (see FIG. 3b) on the side of the electrode opposite the skin contact surface 31. A detent 30 (see FIG. 6) may be formed in the flat back surface 28, and the first contact surface 18 of the electrode may be located in the detent 30. The detent may be defined by an opening 70 (see FIG. 12) in the electrode base pad 16. The electrode base pad 16 may be made of non-conductive materials, such as paper, plastic, fabric, foam, other materials, or a combination thereof. The flat back surface 28 of the base pad 16 may optionally include adhesive material that enables the electrode base pad 16 to adhere to objects. The electrode 14 may include flexible material, thus enabling the electrode 14 to be generally flexible to conform to the contours of the subject's body. The materials of the electrode 14 will be described in more detail later.

As shown in FIG. 3a, the electrode 14 includes the front layer 32 having the skin contact surface 31 of the electrode 14. The skin contact surface 31 is configured to contact the subject's skin and may be defined by a gel layer 34. The gel layer 34 may be conductive and may facilitate the distribution of electric signals between the subject's skin and the electrode 14. The gel layer 34 may include an adhesive material to facilitate the connection between the electrode 14 and the subject's skin. Alternatively, the gel layer 34 may include no adhesive material. A conductive layer or current spreader 36 may be provided on the electrode 14, and the current spreader 36 may be configured to distribute electric signals between the first contact surface 18 of the electrode base pad 16 and the skin contact surface 31 defined by the gel layer 34. The current spreader 36 may be made of, just for example, metallic foils, conductive polymers, graphitized or metallized cloth or wire mesh. The current spreader 36 may generally have a similar shape as the gel layer 34. The current spreader 36 may optionally be smaller than the gel layer 34. Alternatively, the current spreader 36 may be the same size or may be larger than the gel layer 34.

The front layer 32 may also include a non-conductive front portion 38. The non-conductive front portion 38 may optionally be constructed of the same material as the electrode base pad 16. The non-conductive front portion 38 may be made of foam or other materials that provide padding to improve comfort for the subject. In one embodiment, the non-conductive front portion 38 may include an adhesive material that facilitates the connection between the electrode 14 and the subject's skin. It is contemplated that in some embodiments, the non-conductive front portion 38 can be eliminated, and the gel layer 34 may be an adhesive gel capable of adhering the electrode 14 to the subject's skin. In one embodiment, the non-conductive front portion 38 may be positioned around a periphery of the conductive gel layer. That is, an opening 80 (see FIG. 12) having a shape substantially similar to the gel layer 34's may be formed in the non-conductive front portion 38 and the gel layer 34 may be positioned within the opening 80 of the non-conductive front portion 38.

The electrode pad 14 may be provided with a plastic carrier or film to prevent inadvertent and/or premature adhesion of a patient's skin or other object to portions of the front layer 32. The plastic carrier may be removed prior to application of the electrode 14 to the subject's skin. The plastic carrier may be disposed on either one or both of the non-conductive front portion 38 and the gel layer 34 (in embodiments where the gel layer 34 is an adhesive gel). It is contemplated that the electrode pad 16 may be disposable. The electrode pad 16 may be adhered to the subject's skin when in use and after it is no longer needed, the electrode pad 16 may be peeled off from the subject's skin and disposed of. The connector assembly 20 can then be re-used with other electrodes 14.

Figure 4:
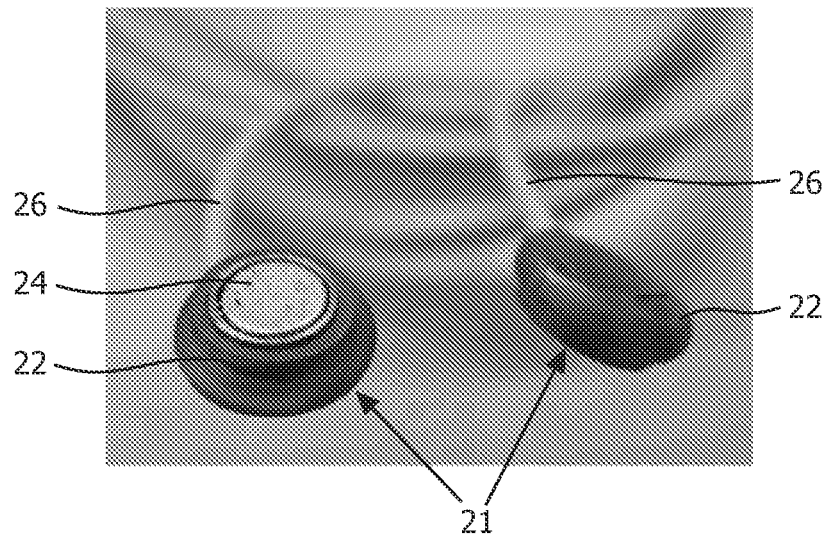
FIG. 4 illustrates a detailed view of an attachment structure of the connector assembly in accordance with one embodiment.
Figure 5:
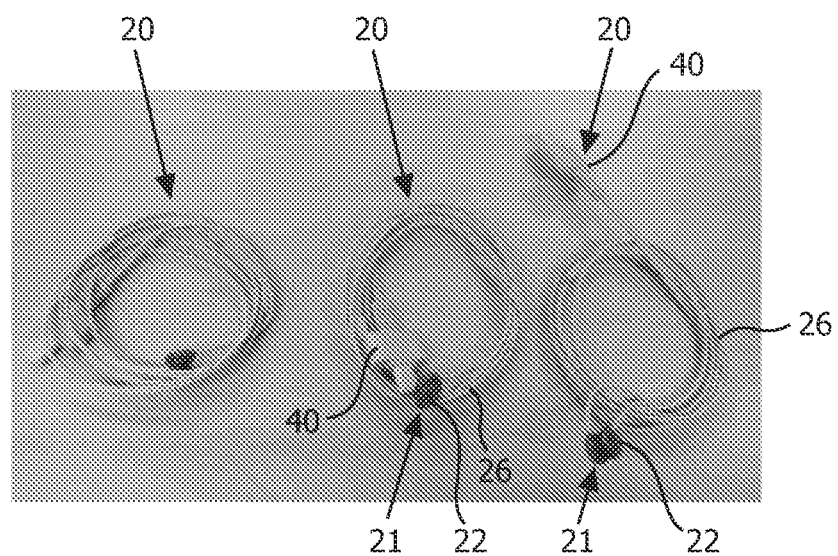
FIG. 5 illustrates the connector assembly in accordance with one embodiment.

FIG. 4 shows the attachment structure 21 of the connector assembly 20 in accordance with one embodiment. In the illustrated embodiment, the housing 22 is configured to hold the second contact surface 24. The second contact surface 24 is disposed in or on the housing 22. The housing 22 is connected to the external electrical apparatus via the electrical connector 26. A connecting structure 40 (see FIG. 5) may be attached to the electrical connector 26 at an end opposite to that of the housing 22. The connecting structure 40 may be configured to releasably connect the connector assembly 20 to the external electrical apparatus. The connecting structure 40 may be a plug, terminal, or other similar structures that enable the connecting assembly 20 to be electrically connected to the external electrical apparatus.

Figure 6:
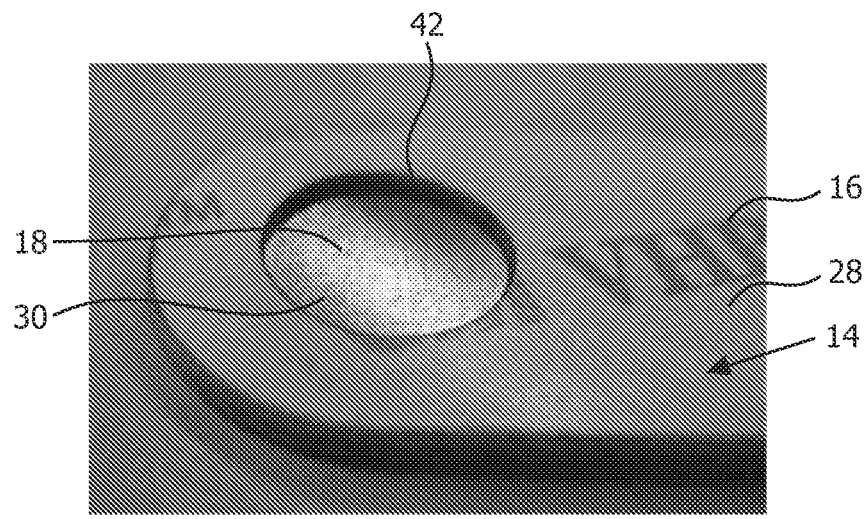
FIG. 6 illustrates a first contact surface of the electrode configured to contact a second contact surface of the connector assembly in accordance with one embodiment.

FIG. 6 is a detailed view of an embodiment of the electrode 14. As mentioned above, the first contact surface 18 is located in the detent 30. The detent 30 may be defined by the opening 70 (see FIG. 12) in the base pad 16. The opening 70 may be circular, rectangular, oval, or any other shapes. The first contact surface 18 is inset of the flat back surface 28 of the base pad 16. Thus, an edge 42 is formed around the periphery of the first contact surface 18. This configuration enables the second contact surface 24 (obstructed from view in this figure) of the connector assembly 20 to be easily aligned with the first contact surface 18 of the electrode pad 16. In particular, the inset of the first contact surface 18 relative to the flat surface of the flat back surface 28 enables the second contact surface 24 to be received in the detent 30, thus ensuring a proper electrical connection between the first contact surface 18 and the second contact surface 24. The edge 42 may prevent the second contact surface 24 from sliding away from its contact with the first contact surface 18. As such, this configuration facilitates and improves the positioning and alignment of the first contact surface 18 and the second contact surface 24. This configuration may also increase user comfort because of the lack of ridges, protrusions, and extra thickness in the electrode 14. Thus, the electrode 14 has a generally flat configuration that enables a subject to lie on it during use (e.g., during sleep).

Figure 7:
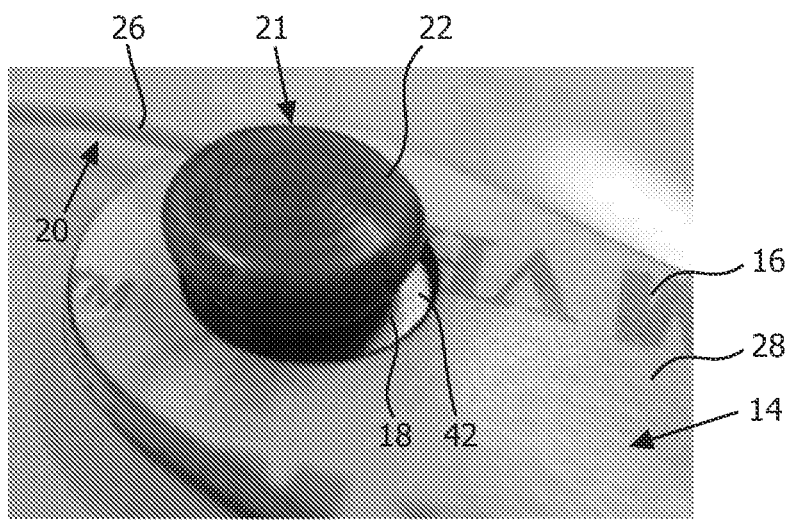
FIG. 7 illustrates a connection between the first contact surface of the electrode and the second contact surface of the connector assembly in accordance with one embodiment.

To establish an electrical connection between the subject's skin and the external electrical apparatus for delivering electrical stimulation to the subject, monitoring the physiological parameter of the subject, or both, the electrode can be connected to the subject's skin via the adhesive material on the front layer 32 of the electrode 14. In some embodiments, either one or both of the gel layer 34 and the non-conductive front portion 38 may provide the adhesive material used to adhere the electrode 14 to the subject's skin. Once the electrode 14 is adhered to the subject's skin, the skin contact surface 31 defined by the gel layer 34 contacts the subject's skin and is electrically connected to the subject's skin. The connector assembly 20 can then be connected to the electrode 14 by magnetically coupling the first contact surface 18 of the electrode 14 with the second contact surface 24 of the connector assembly 20. As mentioned above, either one or both of the first contact surface 18 or the second contact surface 24 may include magnetic material or magnetized material. The second contact surface 24 may be slid along the flat back surface 28 until the second contact surface 24 is aligned with the detent 30 and the first contact surface 18, whereupon the second contact surface 24 magnetically and electrically couples with the first contact surface 18, as shown in FIG. 7. The second contact surface 24 can be operatively connected to the external electrical apparatus via the connector 26 of the connector assembly 20 or the connecting structure 40.

Figure 8A:
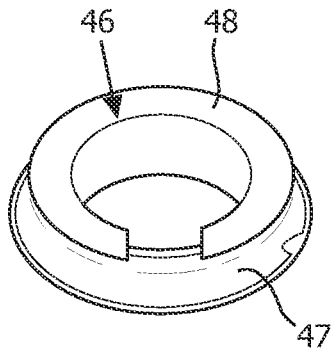
FIGS. 8a-8e illustrate components of the attachment structure of the connector assembly in accordance with an embodiment.
Figure 8B:
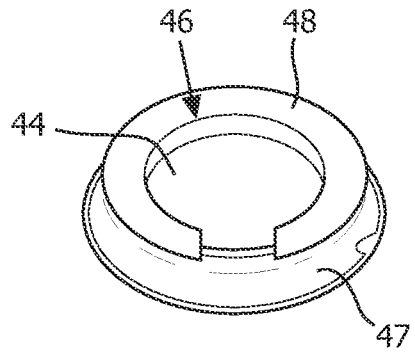

FIGS. 8a-8e illustrate components of the attachment structure 21 of the connector assembly 20 in accordance with an embodiment. In this embodiment, the second contact surface 24 is defined on a permanent magnet. In one exemplary embodiment, the magnet is a Neoflux® magnet. As shown in FIG. 8b, a magnetic material 44 is attached to a metal conductor 46 having a circular configuration. A groove 47 may be provided on the periphery of the metal conductor 46. The magnetic material 44 may be received in the metal conductor 46 such that the metal conductor 46 forms a periphery around the magnetic material 44. The magnetic material 44 may be attached to the metal conductor 46 via adhesives or other attachment mechanisms. The magnetic material 44 may be inset from the metal conductor 46. That is, the top surface of the magnetic material 44 may be situated below the top surface 48 of the metal conductor 46. In one embodiment, the top surface of the magnetic material 44 may be inset from the top surface 48 of the metal conductor 46 by about 0.5 mm. In some embodiments, this configuration of the magnetic material 44 in the attachment structure 21 enables the magnetic material 44 to be at an elevated height with respect to the flat back surface 27 of the base pad 16 when the first contact surface 18 is magnetically coupled to the second contact surface 24. In other words, this configuration of the magnetic material 44 enables the magnetic material 44 to be outside of the detent 30 while the second contact surface 24 is in the detent 30 and is coupled to the first contact surface 18 of the electrode 14. However, it is contemplated that the magnetic material 44 may be positioned in the attachment structure 21 such that the magnetic material 44 is in the detent 30 while the second contact surface 24 is also in the detent 30 and is coupled to the first contact surface 18 of the electrode 14.

Figure 8C:
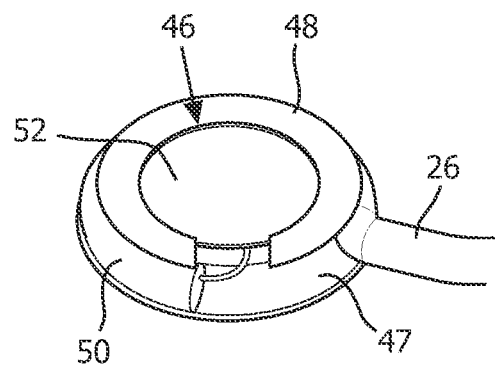
Figure 8D:
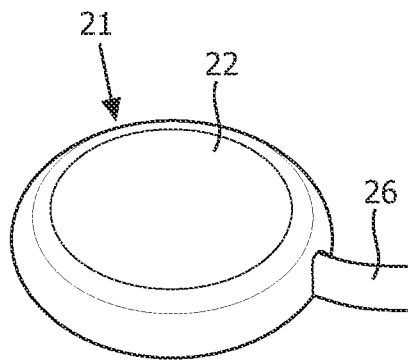
Figure 8E:
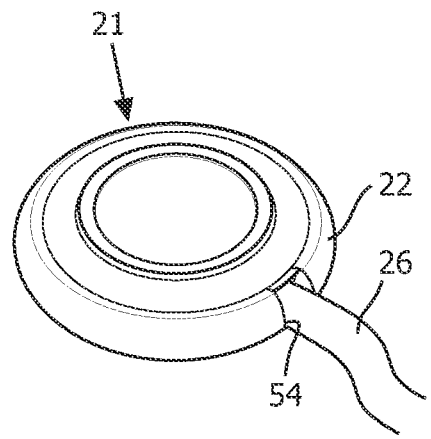

As shown in FIG. 8*c*, an electrical connector, such as an electrical wire 50, may be provided in the groove 47 around the periphery of the metal conductor 46. An end of the electrical wire 50 may be connected to the magnetic material 44 via a conducting adhesive, soldering, or other attachment mechanisms. In one embodiment, the electrical wire 50 may be connected to the top surface of the magnetic material 44. A conductive structure, taking the form of a plate 52 in this embodiment, is placed on top of the magnetic material 44 such that the end of the electrical wire 50 is disposed between the plate 52 and the magnetic material 44. In one embodiment, the electrical wire 50 may be integral to the electrical connector 26. Alternatively, the electrical wire 50 may optionally be a separate wire that is electrically connected to the electrical connector 26. The housing 22 may be placed over the metal conductor 46, plate 52, and magnetic material 44, as shown in FIGS. 8*d*-8*e*, to form the attachment mechanism 21. The connector 26 may extend through a groove 54 provided in the housing 22. When the housing 22 is attached to the metal conductor 46, a portion of the housing 22 may be received in the groove 47 of the metal conductor 46. In some embodiments, the coupling between wire 50 with the metal conductor 46 may be releasable. This may enhance the comfort of the subject, as forces that could cause discomfort to the subject may simply result in disconnection between wire 50 and conductor 46. By way of non-limiting example, wire 50 may be wrapped around the metal conductor 46 in the groove 47 to form a releasable friction interface between wire 50 and metal conductor 46. This may enable the coupling arrangement to be more compact. However, it is contemplated that in some embodiments, the coupling between wire 50 and metal conductor 46 is not releasable.

Figure 1A:
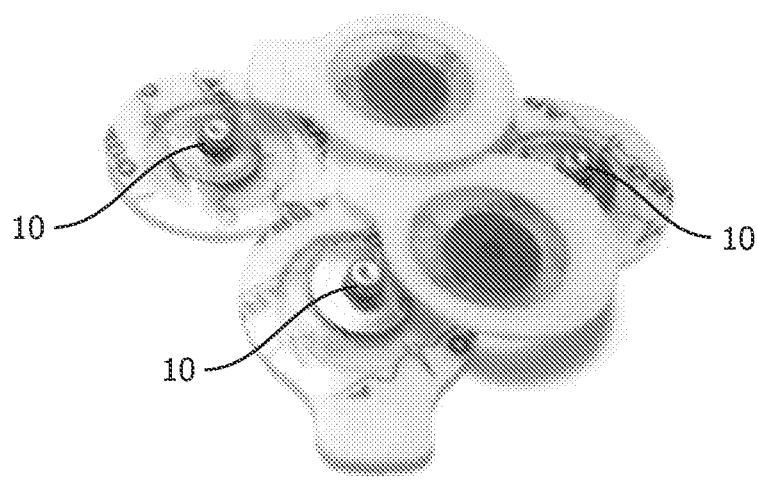
FIGS. 1a-1b illustrate a conventional electrode and conventional connection assembly, respectively, known in the prior art.
Figure 1B:
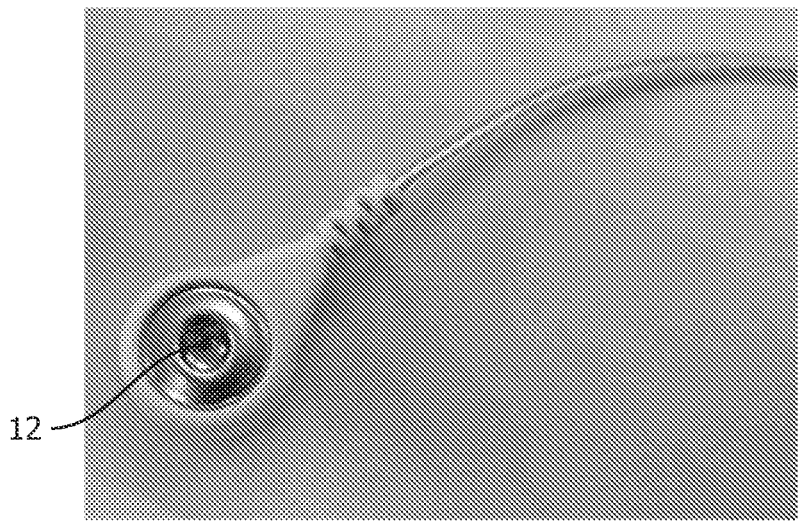
Figure 9:
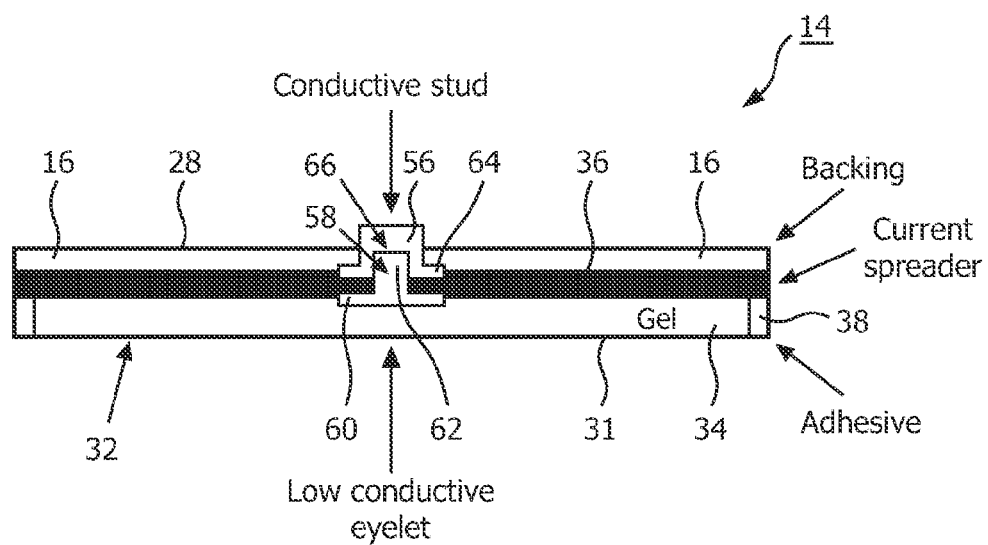
FIG. 9 illustrates a cross sectional view of an electrode having a low conductivity portion in accordance with an embodiment.

FIG. 9 shows a cross section of another embodiment of the electrode 14. In this embodiment, the electrode 14 includes several layers of materials, such as the front layer 32 defined by the gel layer 34 and the non-conductive front portion 38. In this embodiment, the non-conductive front portion 38 is provided with adhesive material to facilitate the connection between the electrode 14 and the subject's skin. The current spreader 36 is provided between the skin contact surface 31 defined by the gel layer 34 and the flat back surface 28 of the base pad 16. A conductive stud 56 is also provided, wherein the conductive stud 56 is configured to engage in a snap-fit connection with the receiving portion 12 (see FIG. 1*b*) of another embodiment of the connector assembly 10. In the illustrated embodiment of the electrode 14, an eyelet 58 is configured to be fixed to the stud 56. In this embodiment, the stud 56 may be considered the first contact surface 18. That is, in some embodiments that have the stud 56, the stud 56 may be magnetically coupled to a portion of the connector assembly 20. In embodiments wherein the electrode 14 is used for stimulation purposes, the stud 56 may receive electric signals from the connector assembly 20 and conduct the electric signals to the current spreader 36, which distributes the electric signals to the gel layer 34. The gel layer 34 may then distribute the electric signals to the subject's skin.

In the illustrated embodiment, the eyelet 58 has a head 60 in contact with the current spreader 36 and the gel layer 34. Additionally, the eyelet 58 has a shaft 62 that extends through the current spreader 36 and into the base pad 16. In the illustrated embodiment, the stud 56 has a head 64 that contacts the current spreader 36 and the base pad 16. Additionally, the stud 56 has a shaft 66 that extends through and out of the base pad 16 so that the stud 56 may be engaged in a snap-fit connection with the connector assembly 20. The eyelet 58 may also optionally be friction fitted, riveted or crimped into the stud 56. As mentioned above, if the eyelets 58 are made of conductive materials, such as metal or covered with metallic conductive materials, this configuration may create "hot spots" due to the highly conductive nature of the eyelets 58 and due to uneven electrode-skin contact. For example, if the eyelet 58 is constructed from highly conductive materials, the shorter distance between the head 60 of the eyelet 58 and the subject's skin relative to the distance between the current spreader 36 and the subject's skin may cause uneven current distribution and "hot spots".

In the embodiment shown in FIG. 9, the eyelet 58 includes materials having a lower conductivity than that of metals, such as, for example, plastic. In some embodiments, the eyelet 58 includes non-conductive materials. In one embodiment, the eyelet 58 is a carbon-filled plastic eyelet. The stud 56 may be made of conductive materials, such as metal. In one embodiment, the stud 56 is made of a metal material having silver coating. Thus, in this embodiment, the eyelet 58 has a lower conductivity than that of the stud 56 and the current spreader 36. This configuration and characteristics of the eyelet 58 and the stud 56 may eliminate high current density at the position of the eyelet 58, thus avoiding "hot spots".

Figure 10:
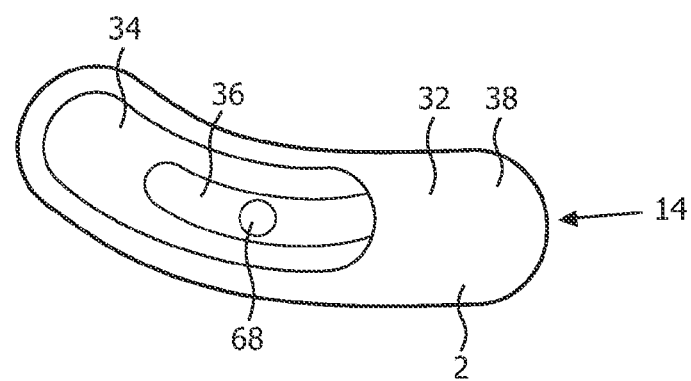
FIG. 10 illustrates the low conductivity portion of the electrode in accordance with an embodiment.

In the embodiment shown in FIG. 10, the current spreader 36 includes a low conductive portion 68 having an area smaller than that of the current spreader 36. The low conductive portion 68 may comprise a material having a lower conductivity than that of the rest of the current spreader 36. In one embodiment, the low conductive portion 68 may be disposed within the current spreader 36 or may be a separate piece attached to the current spreader 36. In one embodiment, the current spreader 36 may surround the low conductive portion 68 such that the low-conductivity portion 68 is situated like an "island" within or on the current spreader 36. In one embodiment, the low conductive portion 68 may cover the current spreader 36 similar to the head 60 of the eyelet 58 shown in FIG. 9. Accordingly, the low conductive portion 68 may reduce the chances of or avoid the occurrence of "hot spots." In one embodiment, the low conductive portion 68 may be made of plastic. The size, shape, or configuration of the low conductive portion 68 may vary.

Figure 11:
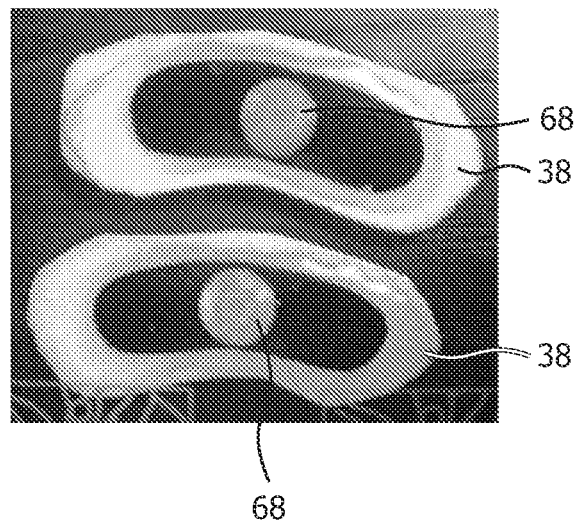
FIG. 11 illustrates low-conductivity or non-conductive portions of the electrode in accordance with one embodiment.

As shown in FIG. 11, the electrode 14 may have non-conductive or low-conductive portions, including the non-conductive front portion 38 and the low-conductive portion 68. In embodiments where the electrode 14 includes the stud 56 and the eyelet 68, the low-conductive portion 68 may be the eyelet 58. Alternatively, the low-conductive portion 68 may be a portion of the current spreader 36 that is either non-conductive or has low-conductive properties. The low-conductive portion 68 may be a low conductive material within the current spreader 36 or may be attached to the current spreader 36.

Figure 12:
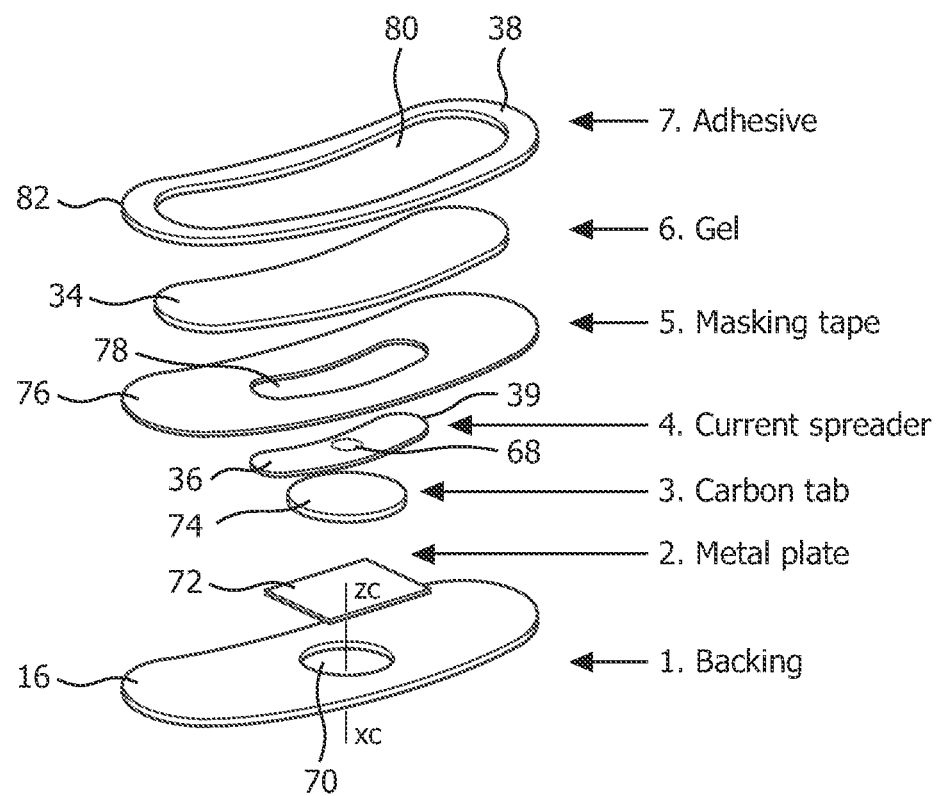
FIG. 12 is an exploded view of components of the electrode in accordance with an embodiment.

FIG. 12 shows an exploded view of the various layers or materials of the electrode 14 in accordance with one embodiment. In this embodiment, the electrode 14 includes the base pad 16 having the opening 70 that defines the detent 30 configured to receive the first contact surface 18 of the connector assembly 20. In this embodiment, the base pad 16 is generally banana-shaped, although circles, rectangles, or other shapes are contemplated. The base pad 16 may include foam material, such as the polyolefin type made by Sekisui.

In the illustrated embodiment, a plate 72 is disposed on the base pad 16, wherein the first contact surface 18 is defined on the plate 72. That is, the first contact surface 18 may be a portion of the plate 72 that is exposed through the opening 70. In the illustrated embodiment, the plate 72 is rectangular.

Alternatively, the plate 72 may be circular, banana-shaped, or may be other shapes. In this embodiment, the plate 72 is a metal plate, such as those made by Hasberg-Schneider GmbH. In some embodiments, the plate 72 may include a magnet or may include ferromagnetic material. In such embodiments, the plate 72 may include magnetic characteristics or may be magnetized to include magnetic characteristics that enables the plate 72 to be magnetically coupled to metals or other magnetic materials. In such embodiments, the second contact surface 24 of the connector assembly 24 may include metal.

A second conductive layer 74 may be disposed on the plate 72. The second conductive layer 74 may be configured to conduct electric signals between the current spreader 36 and the first contact surface 18 defined on the metal plate 72 and may be made of carbon or other conductive materials. The second conductive layer 74 may be circular, rectangular, banana-shaped, or may be other shapes. The second conductive layer 74 may also include adhesive material that enables the second conductive layer 74 to be adhered to other portions of the electrode 14. The second conductive layer 74 may be a carbon disk, such as those made by SPI Supplies/Structure Probe, Inc.

The current spreader 36 may be disposed on the second conductive layer 74 and may be configured to distribute electric signals between the second conductive layer 74 and the gel layer 34. In some embodiments, the current spreader 36 may be disposed on the metal plate 72 and may define a portion of the first contact surface 18 such that when the second contact surface 24 of the connector assembly 20 is magnetically and electrically coupled to the first contact surface 18 of the metal plate 72, the current spreader 36 is disposed between the metal plate 72 and the second contact surface 24 of the connector assembly 20. The current spreader 36 may have edges 39. In the illustrated embodiment, the current spreader 36 is generally banana-shaped. Alternatively, the current spreader 36 may be circular, rectangular, or may be other shapes. The current spreader 36 may include conductive materials such as those made by Exopack. An electrically insulating material 76, taking the form of a tape in this embodiment, may be provided with an opening 78 configured to receive or overlap the current spreader 36. In some embodiments, the electrically insulating material 78 may include adhesive material. The insulting material 76 may be a double-sided tape having adhesives on both surfaces thereof, such as those made by Tesa Tape, Inc. The opening 78 may be shaped substantially similar and may also be sized substantially similar to the current spreader 36. As such, the current spreader 36 may be exposed through the opening 78. In the illustrated embodiment, the insulating material 76 is generally banana-shaped. Alternatively, the insulting material 76 may be circular, rectangular, or may be other shapes. Portions of the insulating material 76 may contact and adhere to portions of the base pad 16, thus retaining materials and layers therebetween.

The gel layer 34 may be disposed on the insulating material 76. In the illustrated embodiment, the gel layer 34 is generally banana-shaped. Alternatively, the gel layer 34 may be circular, rectangular, or may be other shapes. The gel layer 34 may include hydrogel materials, such as, just for example, the ARBO HRA5 gel made by Covidien. In the illustrated embodiment, the non-conductive front portion 38 includes the opening 80 configured to receive the gel layer 34. As mentioned above, in some embodiments, the non-conductive front portion 38 may be eliminated from the electrode 14 and the gel layer 34 may be used to adhere the electrode 14 to the subject's skin. In this embodiment, the non-conductive front portion 38 is provided with adhesive material on a top surface 82 thereof, wherein the top surface 82 of the non-conductive front portion 38 contacts and adheres to the subject's skin. The non-conductive front portion 38 may include adhesive materials such as those made by Smith & Nephew. In one embodiment, the gel layer 34 may be received in the opening 80 of the non-conductive front portion 38 such that the non-conductive front portion 38 is flush with the gel layer 34. That is, the top surface 82 of the non-conductive front portion may be substantially even with the skin contact surface 31 of the gel layer 34. In some embodiments that have the non-conductive portion 38 with adhesive material, the gel layer 34 may optionally be non-adhesive. Forming the non-conductive portion 38 with adhesive material around the periphery of the gel layer 34 may improve the fixation or connection of the electrode 14 to the subject's skin and may also improve the conductive performance of the gel layer 34.

The size of the current spreader 36 or the skin contact surface 31 and the amount of electrical power that is applied during stimulation can significantly influence a subject's comfort. For example, in some situations, the subject may experience tingling or other sensations that may cause discomfort. These tingling sensations may be due to the stimulations of neurons that are incidentally stimulated along with the targeted muscles. Furthermore, subjects often experience the most discomfort at the leading edges of the electrode 14, also known as the "edge effect."

In the embodiment shown in FIG. 12, the gel layer 34 is shaped generally similar to the current spreader 36 and has a larger size than the current spreader 36 such that the gel layer 34 overlaps the current spreader 36. The gel layer 34 may extend a predetermined distance over the edges 39 of the current spreader 36. For example, in some embodiments, the predetermined distance that the gel layer 34 extends over the edges 39 of the current spreader 36 may be greater than a thickness of the gel layer 34. This configuration of the gel layer 34 and current spreader 36 avoids the edge effect and thus decreases the tingling or other uncomfortable sensations experienced by the subject.

Figure 13:
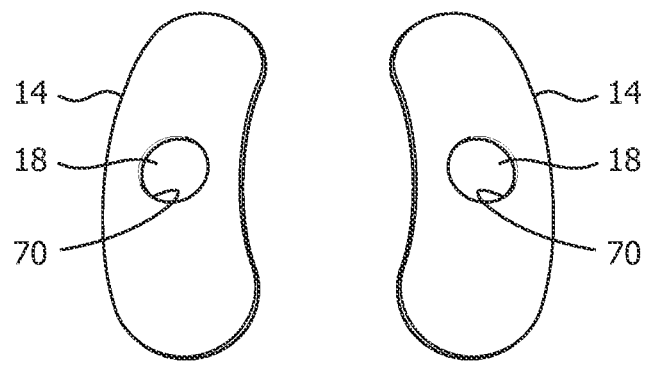
FIG. 13 illustrates the base pad opposite the side of the electrode having the subject contact surface, in accordance with an embodiment.

FIG. 13 shows an embodiment of the electrode 14. In this embodiment, the opening 70 and the first contact surface 18 is located centrally of the base pad 16. It is contemplated that the opening 70 may be located at other locations and may vary in size and location.

Figure 14:
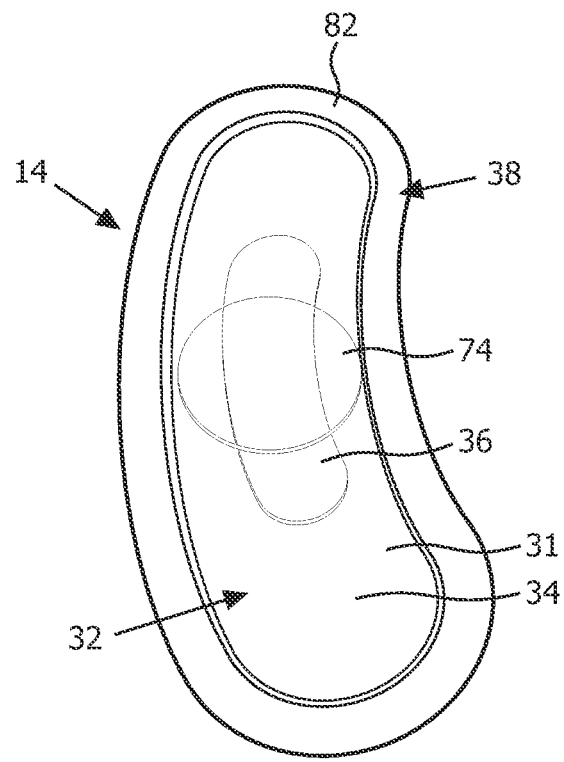
FIG. 14 illustrates a front layer of the electrode having the subject contact surface in accordance with an embodiment.

FIG. 14 shows the front layer 32 of the electrode 14 in accordance with the embodiment shown in FIG. 12. In this embodiment, the non-conductive front portion 38 is configured to contact the subject's skin and includes adhesive material configured to adhere the electrode 14 to the subject's skin. The front layer 32 of the electrode 14 is defined by the non-conductive front portion 38 and the gel layer 34. The top surface 82 of the non-conductive front portion 38 is flush or detents slightly with the skin contact surface 31 defined by the gel layer 34. In this embodiment, the current spreader 36 is positioned between the gel layer 34 and the second conductive layer 74 so that the current spreader 36 can conduct electric signals between the second conductive layer 74 and the gel layer 34. The current spreader 36 is shaped substantially similar to the gel layer 34 and has a smaller size than the gel layer 34. As such, the gel layer 34 is configured to overlap the current spreader 36.

The size, shape, and configuration of the electrode 14 may vary in various embodiments. For example, in one embodiment, the electrode 14 may include more than one first contact surface 28. As such, a plurality of attachment structures 21 of the connector assembly 20 may be used to create connections between the connector assembly 20 and the first contact surfaces 28 of the electrode 14. In some embodiments, a plurality of connector assemblies 20 may be connected to a single electrode 14 that has a plurality of first contact surfaces 28.

It is also contemplated that one or more sensors may be provided on the electrodes 14. For example, a temperature sensor, motion sensors, microphone, oximetry sensor, or any combination thereof can be provided for detecting various physiological parameters of the user. The output of these sensors can be used to control the stimulation therapy provided to the user, stored for monitoring purposes, transmitted to a remote location, or any combination thereof. It is also contemplated that in some embodiments, the one or more sensors may be provided on the connector assembly 20. The connector assembly 20 may be connected to the external electrical apparatus wirelessly instead of using a wire. In such wireless embodiments, electric signals and information may be transferred between the connector assembly 20 and the external electrical apparatus wirelessly, such as via RF frequency, IR frequency, or other frequencies. In such embodiments, the connector assembly 20 may include a power source and/or a transceiver. Accordingly, in such embodiments, the transceiver may be considered the electrical connector 26. The connector assembly 20 and the electrode 14 may transfer signals between each other via the magnetic and electrical coupling, as described above.

The electrode assembly 13 may be used in a variety of ways and are not limited to the ones described. It is contemplated that the electrode assembly 13 can be used to deliver energy, monitor one or more of a variety of physiological parameters of the subject, such as electro-physiological impedance signals, physiological resistance, or any combination thereof. Other parameters that can be monitored include galvanic skin responses and ear-to-ear impedance changes.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An electrode assembly comprising:
   an electrode configured to provide electrical contact with a subject's skin through a subject contact surface, the electrode comprising an electrode base pad having a first contact surface;
   a connector assembly configured to electrically connect the electrode to an external electrical apparatus to transfer electrical signals between the subject's skin and the external electrical apparatus, the connector assembly comprising:
      a housing having a second contact surface, the second contact surface being configured to be magnetically and electrically coupled to the first contact surface of the electrode base pad; and
      an electrical connector configured to connect the second contact surface to the external electrical apparatus;
   a gel layer that forms the subject contact surface; and
   a current spreader disposed between the first contact surface and the subject contact surface formed by the gel layer, wherein the current spreader is directly connected to the first contact surface of the electrode base pad, and wherein the current spreader is directly connected to the gel layer forming the subject contact surface, and wherein the current spreader includes a conductive layer.

2. The electrode assembly of claim 1, wherein the gel layer has lower conductivity than the current spreader, and wherein the current spreader includes at least one of a metallic foil, a conductive polymer, graphitized cloth, metalized cloth, or wire mesh.

3. The electrode assembly of claim 2, wherein the gel layer has a larger area than the current spreader.

4. The electrode assembly of claim 1, wherein the electrode is generally in a shape of a banana.

5. The electrode assembly of claim 1, wherein the current spreader includes a low-conductivity portion having an area smaller than that of the current spreader, and wherein the low-conductivity portion comprises a material having a lower conductivity than that of the rest of the current spreader.

6. A method for providing electrical contact with a subject's skin using an electrode assembly that includes an electrode, a connector assembly, a gel layer that forms a subject contact surface, and a current spreader, the method comprising:
   connecting the electrode to the subject's skin, the electrode comprising a subject contact surface and an electrode base pad having a first contact surface, wherein connecting the electrode to the subject's skin includes electrically coupling a current spreader between the first contact surface and the subject contact surface, wherein:
      the current spreader includes a conductive layer;
      the current spreader is directly connected to the gel layer forming the subject contact surface; and
      the current spreader is directly connected to the first contact surface of the electrode base pad;
   coupling the first contact surface of the electrode base pad to a second contact surface of the connector assembly, the second contact surface located on a housing of the connector assembly, and the coupling provided magnetically; and
   connecting the second contact surface of the connector assembly to an external electrical apparatus to transfer electrical signals between the subject's skin and the external electrical apparatus, the connection provided by an electrical connector of the connector assembly.

7. The method of claim 6, wherein the gel layer has lower conductivity than the current spreader, and wherein the current spreader includes at least one of a metallic foil, a conductive polymer, graphitized cloth, metalized cloth, or wire mesh.

8. The method of claim 7, wherein the gel layer has a larger area than the current spreader.

9. The method of claim 6, wherein the electrode is generally in a shape of a banana.

10. The method of claim 6, wherein the current spreader includes a low-conductivity portion having an area smaller than that of the current spreader, and wherein the low-conductivity portion comprises a material having a lower conductivity than that of the rest of the current spreader, and wherein connecting the second contact surface of the connector assembly to the external electrical apparatus includes delivering an electrical stimulus to the subject with a reduced chance of an occurrence of a hot spot by virtue of the low-conductivity portion.

11. An electrode assembly, comprising:
   means for connecting an electrode to a subject's skin, the electrode comprising, a subject contact surface, and an electrode base pad having a first contact surface;

means for coupling, magnetically, the first contact surface of the electrode base pad to a second contact surface of the means for coupling, the second contact surface located on a housing of the means for coupling;

means for connecting the second contact surface of the means for coupling to an external electrical apparatus to transfer electrical signals between the subject's skin and the external electrical apparatus; and means for spreading current disposed between the first contact surface and the subject contact surface, wherein:
  the subject contact surface is formed by a gel layer;
  the means for spreading current is directly connected to the first contact surface and includes a conductive layer; and
  the means for spreading current is directly connected to the gel layer forming the subject contact surface.

12. The electrode assembly of claim 11, wherein the gel layer has lower conductivity than the means for spreading current, and wherein the means for spreading current includes at least one of a metallic foil, a conductive polymer, graphitized cloth, metalized cloth, or wire mesh.

13. The electrode assembly of claim 12, wherein the gel layer has a larger area than the means for spreading current.

14. The electrode assembly of claim 11, wherein the electrode is generally in a shape of a banana.

15. The electrode assembly of claim 11, wherein the means for spreading current includes a low-conductivity portion having an area smaller than that of the means for spreading current, and wherein the low-conductivity portion comprises a material having a lower conductivity than that of the rest of the means for spreading current.

\* \* \* \* \*